US007851425B2

(12) United States Patent
Baquete et al.

(10) Patent No.: US 7,851,425 B2
(45) Date of Patent: Dec. 14, 2010

(54) PLASTICIZED ARTICLE FOR TREATING THE SKIN

(75) Inventors: Katia Cristina Baquete, Valinhos (BR); Paula Fabiana de Campos Silva, Trumbull, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 393 days.

(21) Appl. No.: 11/794,017

(22) PCT Filed: Nov. 7, 2005

(86) PCT No.: PCT/EP2005/011970

§ 371 (c)(1), (2), (4) Date: Jun. 2, 2008

(87) PCT Pub. No.: WO2006/066655

PCT Pub. Date: Jun. 29, 2006

(65) Prior Publication Data

US 2009/0082239 A1 Mar. 26, 2009

(30) Foreign Application Priority Data

Dec. 22, 2004 (BR) .................................... 0405865

(51) Int. Cl.
*A61K 7/50* (2006.01)

(52) U.S. Cl. ....................... 510/141; 510/148; 510/152; 510/155

(58) Field of Classification Search ....................... None
See application file for complete search history.

(56) References Cited

U.S. PATENT DOCUMENTS

| | | | |
|---|---|---|---|
| 5,510,050 | A | 4/1996 | Dunbar et al. |
| 5,834,410 | A | 11/1998 | Slocum et al. |

(Continued)

FOREIGN PATENT DOCUMENTS

| | | |
|---|---|---|
| DE | 198 49 901 | 5/2000 |

(Continued)

OTHER PUBLICATIONS

International Search Report, PCT/EP2005/011970, mailed Mar. 6, 2006, 2 pp.

(Continued)

*Primary Examiner*—Necholus Ogden, Jr.
(74) *Attorney, Agent, or Firm*—Alan A. Bornstein

(57) ABSTRACT

Articles for treating the skin having high plasticity and low ware rate are described. Articles herein described are proper for treating the skin by rubbing them onto the skin, for example, in the form of a soap bar presenting increased plasticity and low rate of wear. The preferred embodiment is an article that has one or multiple projections arising from at least one surface of a first body are described. The first body and the projections are a thermoplastic mass that includes a surfactant suitable for cleansing skin and a plasticizing agent. The articles are especially suited for projection bars used to be applied onto the skin for either cleansing or massaging or both at the same time. Robust and economical projection bars are described that can be efficiently manufactured by the careful selection of the plasticity, wear rate and rheological properties of the masses of the first body and projections.

17 Claims, 2 Drawing Sheets

U.S. PATENT DOCUMENTS

| | | | |
|---|---|---|---|
| 6,491,933 | B2 | 12/2002 | Lorenzi et al. |
| 6,495,151 | B2 | 12/2002 | McAtee et al. |
| 6,730,642 | B1 | 5/2004 | Aronson et al. |
| 6,949,494 | B2 | 9/2005 | Clignet |
| 2004/0109720 | A1 | 6/2004 | Gruenbacher et al. |

FOREIGN PATENT DOCUMENTS

| | | |
|---|---|---|
| FR | 2 187 904 | 1/1974 |
| GB | 1 469 131 | 3/1977 |
| RU | 2 171 833 | 8/2001 |
| WO | 92/13060 | 8/1992 |

OTHER PUBLICATIONS

GB Search Report, GB0516417.3, dated Jan. 9, 2006, 1 p.

Pursuant to MPEP § 2001.6(b) applicants bring the following co-pending application to the Examiner's attention: Applicant: Sant'Ana Caceres, et al. Case No. J3785(C) U.S. Appl. No. 11/794,018, filed Jun. 21, 2007 For: Plasticized Article for Treating the Skin.

PLASTICIZED ARTICLE FOR TREATING THE SKIN

This invention relates to plasticized articles used for treating the skin. The articles of the invention include personal cleansing bars that include one or more projections arising from a main body. The projections are made with a thermoplastic mass that comprises a surfactant suitable for cleansing the skin, and a plasticizing agent. The articles of the invention are especially suitable for providing treatment to the skin, such as for example cleansing, massaging or both at the same time.

Consumers are increasingly receptive to articles used for treating the skin in various manners. Articles that are able to provide either personal cleansing or massaging or both and even having additional skin benefits, new sensory experiences, novelty, or generally create a more pleasurable sensory experience during the treatment can be used in showering and bathing. For example, cleansing bars and implements that offer moisturization, exfoliation, massaging action and skin toning have been embraced by consumers.

With the resurgence of the specialty soap and personal care market exemplified by various personal care boutiques, personal washing bars that have more complex shapes and structures are being offered. One example is the so-called massaging bar, characterized by having protrusions or nubs of various shapes emanating from a common surface. A second example is bar that has an embossed projection that resembles a common object such as a cartoon character, which is especially suitable for children and fosters personal hygiene.

Current "projection bars", i.e., bars such as those for cleaning purposes bars that have one or more projections emanating from at least one common surface, are virtually all made either by hand casting or hand stamping. Thus, these articles are essentially confined to a specialty market with limited distribution, and much higher selling price. However, it would be desirable to offer such bars to a wider range of consumers in the mass market.

Several problems arise in the design of projection bars for the mass market. The first problem concerns robustness. Mass market bars are subjected to more mechanical shock both during distribution where they are often thrown into large bins, and in routine use where they may be inadvertently dropped. The inventors have found that by incorporating a plasticizer at a sufficient level in the mass from which the projections are made, the projections, especially if they are long, will be far less prone to fracture and separate from the cleansing article.

A second problem encountered is related to wear away during use. When the bar is directed to cleansing, produced by normal cast-melt compositions such as well known glycerin soaps, they usually present a high wear rate. When such compositions are used to make projection bars, as is frequently the case, the projections wear away quickly, and the consumer is left with an ordinary soap. Thus, the benefits of the projections, e.g., for a massaging action, are quickly lost.

The third problem encountered in adapting projection bars to mass market applications is efficient low-cost manufacture. Operationally, this means that the solid or semi-solid mass or masses from which the projection bar is derived must be capable of extrusion. Further, this extruded mass should be capable of automated stamping in a projection bar mold, and automated packing to achieve a production rate of at least 25 tablets or bars per minute, preferably at least about 50 bars per minute and more preferably at least about 100 bars per minute.

U.S. Pat. No. 6,730,642 discloses soaps having an artisan crafted appearance combining a first and a second solid mass in a continuous and discontinuous relationship. Plasticizing agents are disclosed in order to achieve proper dispersion of the second solid mass within the first solid mass.

U.S. Pat. No. 5,510,050 discloses plasticizers that are solid at room temperature but liquid at process temperature (e.g. temperature of extrusion) for use in a bar composed predominantly of sodium cocoyl isethionate.

United States Patent Publication No. 2004/0109720 discloses a personal care article in the form a disposable applicator comprising a multilayered substrate containing a fluid which is useful for applying cosmetic lotions and creams.

U.S. Pat. No. 6,491,933 discloses a personal care article comprising a hot melt composition. The article includes a water insoluble substrate of a creped non-woven layer, and a cleansing composition that meets certain rheological and composition requirements.

U.S. Pat. No. 6,495,151 discloses disposable cleansing articles for skin and hair that are composed of a water insoluble substrate that contains apertures of certain size and frequency, and a lathering surfactant releasably associated with the substrate.

The present invention seeks improvements over deficiencies in the known art by conveniently managing characteristics of the bar, such as plasticity and rate of wear, usefully to be controlled for many articles for treating the skin (particularly given the known sensitivity of human skin).

When the article is a soap bar such characteristics become more important, and yet more prominently when the article is a soap bar of the type provided with one or more projections or protrusions arising out of one of its surfaces.

Among the one or more problems addressed include increasing the plasticizing characteristic of the article without increasing its wear rate; producing projection bars that are more resistant to fracture during handling and inadvertent misuse; producing projection bars that have lower wear rates thus maintaining the projections for longer time during use; and producing projection bars having rheological properties that allow efficient automated manufacture.

The subject invention describes an article for treating skin having increased plasticizing characteristics without having increased wear rate. In one preferred embodiment, the article includes projections or protrusions that are made from a solid or semi-solid surfactant mass that are more resistant to fracture during distribution and/or inadvertent misuse and have lower wear rate.

More specifically, in an embodiment the article for treating skin includes a first body and one or a multiplicity of projections arising from at least one surface of said first body, wherein the first body and the projections are made from extruded thermoplastic masses, called respectively the first body mass and the projections mass, wherein both masses include a surfactant suitable for contact with human skin (but not necessarily the same). Besides the surfactants, the projections mass includes a plasticizing agent ingredient which is optional for the first body mass.

In a second embodiment, the projection mass has an intrinsic wear rate less than about 33%, preferably less than about 31%, more preferably less than about 30% and most preferably less than about 28% as measured by the Controlled Rubbing Test.

In another embodiment, both the first body mass and the projection mass have a hardness value measured at a temperature in the range from 38° C. to 42° C. of at least about 20 lbs/in$^2$ (137.9 kPa), and preferably at least about 28 lbs/in$^2$ (193 kPa) as measured by the Cylinder Impaction Test described in the Evaluation Methodology section below. To convert to SI units 1 lbs/$in^2$ is equal to 6.895 kPa.

In another embodiment, the level of plasticizing agent included in the projection mass is sufficient for the projection mass to have a Plastic Index Value of at least about 7 mm, preferably about 7 mm to about 14 mm and most preferably about 7 mm to about 12 mm, as measured by the Three Point Bending Test.

Another embodiment, the article of the current invention is especially useful for the simultaneous cleansing and massaging of the skin. Specifically, this article includes a first body and a multiplicity of projections arising from a surface of the first body, wherein the projections have an elevation above a surface defining an average surface of the first body between about 5 mm to about 20 mm, preferably 7 mm to about 18 mm and most preferable about 7 mm to about 15 mm, and wherein the first body and the projections are made from extruded thermoplastic masses, called respectively the first body mass and the projections mass, wherein both masses include a surfactant suitable for contact with human skin (but not necessarily the same surfactant), and wherein the projection mass includes a plasticizing agent. The plasticizer is chosen to provide an increased robustness of the projection bar relative to plain soap, and also can reduce the rate of wear of the projections.

Still other embodiments and applications of the present invention will become clear from the following description of the invention.

The invention will be described by way of example only with reference to the accompanying drawings, in which:

FIG. 2 contains schematic diagram illustrating various projection bars that have different types of projections and shapes;

Figure 1:
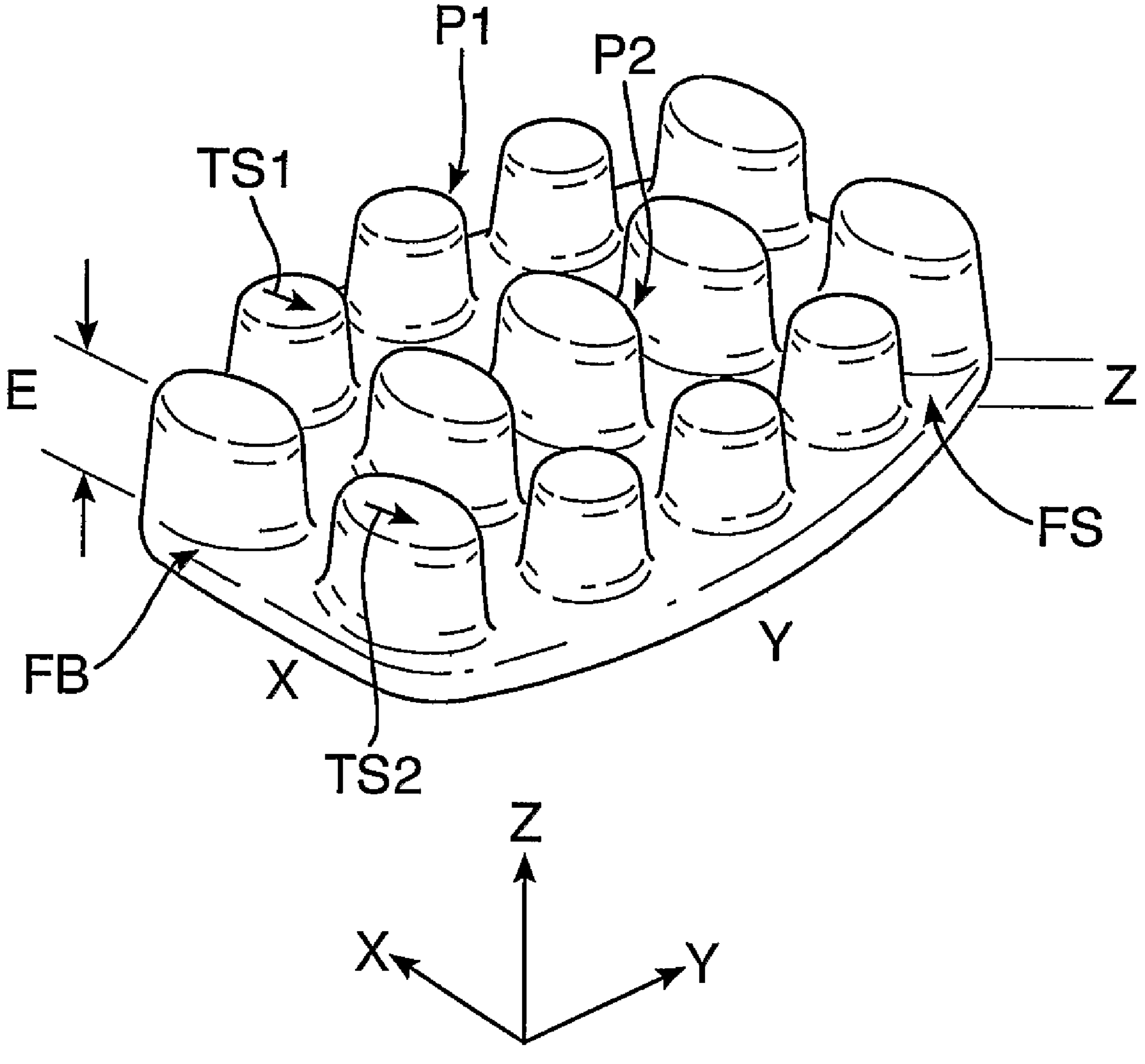
FIG. 1 is a schematic diagram depicting a projection bar and the various parameters used to define its geometrical characteristics.

As used herein % or wt % refers to percent by weight of an ingredient as compared to the total weight of the composition or component that is being discussed.

Except in the operating and comparative examples, or where otherwise explicitly indicated, all numbers in this description indicating amounts of material or reaction conditions, physical properties of materials and/or use are to be understood as modified by the word "about". All amounts are by weight of the final composition, unless otherwise specified.

It should be noted that in specifying any range of concentration, any particular upper concentration can be associated with any particular lower concentration.

For the avoidance of doubt the word "comprising" is intended to mean "including" but not necessarily "consisting of" or "composed of". In other words, the listed steps or options need not be exhaustive.

In this invention the word "treating" shall be construed as including either cleansing or massaging or both at the same time, and/or even providing any further benefit to the skin, as better appreciated and enhanced by each individual user and as hereinafter described in the present invention.

The present invention also relates to an article for treating skin that includes a first body and one or more projections arising from at least one surface of this first body, wherein the projections are made from a solid or semi-solid surfactant mass, called the surfactant mass of the projections, that includes a surfactant suitable for contact with human skin and a plasticizing agent. A detailed description of the components of the invention is given below.

The first body of the instant cleansing article is the component to which the projections are affixed, and is the means by which the article is gripped and held during cleansing.

The first body can be made from a variety of materials and can have a variety of shapes and conFig.urations.

In a preferred embodiment, the first body and the projections are both made from a thermoplastic water soluble or water erodable (i.e., dispersible) solid that include one or more skin compatible surfactants as a predominant ingredient. The mass of the first body can be either of the same or different chemical composition as the material making up the mass of the projections. By "thermoplastic solid" is meant a solid that softens above a particular temperature or temperature range to form preferably a highly viscous mass, e.g., a liquid and or a putty consistency. In the case were the solid forms a highly viscous mass above its softening point, the mass can be milled and/or mixed, extruded, and shaped into a desired form and then cooled. If a liquid is formed, the liquid can be poured into a mold, solidified, and if desired further shaped into the final article or implement.

In an especially preferred embodiment, the mass of the first body and the mass of the projections are thermoplastic masses that are extrudable. By "extrudable" is meant that the masses can be mixed and blended in conventional mills and plodders used in soap production. It has been found that to be processable (e.g. extrusion, stamping and wrapping) at the desired rate the two masses should have certain mechanical properties at the extrusion temperature that is generally in the range of 38° C. to 42° C. In particular, the hardness of the two masses measured at a temperature in the range from 38° C. to 42° C. should be at least about 20 lbs/$in^2$ and preferably at least about 28 lbs/$in^2$ as measured by the Cylinder Impaction Test described in the Evaluation Methodology section below.

Various types of materials can be used to form a suitable thermoplastic water soluble or water erodable solid for the first body. Such materials include surfactants such as fatty acid soaps, synthetic surfactants, commonly called "syndets", or combinations thereof. These surfactants can be used alone or in combination with solid binders such as polyalkaline oxides (e.g., polyethylene oxide), fatty acids (e.g., stearic acid), waxes (e.g., ester or hydrocarbon waxes) or mixtures of their mixtures. However, when binders are used, they should be chosen so as to avoid undesirable increase in the protrusions wear rate.

The specific types of surfactants that can be used to form the thermoplastic mass of the first body as well as the protrusions are described in the Surfactants Section.

The thermoplastic surfactant mass of the first body can be shaped into regular geometric forms such as a prismoidal section, a cylindrical section, an oblate or prolate spheroidal section, a toroidal section and the like. Alternatively, the first body can be dog-bone shaped, doughnut shaped or can have a more abstract shape.

In another embodiment the first body can be composed of a water insoluble solid material fabricated into a desired shape and affixed with one or more projections meeting the criteria described below. Suitable insoluble materials include molded plastics like polyethylene and polypropylene.

In still another embodiment, the first body could be a woven or non-woven fabric or a sponge like material fashioned into a flexible cloth or a more rigid scrim or pad. Such fabric or sponge-like materials suitable for personal cleansing applications are well known in the art.

An extrudable thermoplastic material containing at least one skin compatible surfactant is the preferred mass of the first body.

Generally, the first body makes up about 40% to about 95% of the cleansing article by weight, preferably at least about 50% by weight and most preferably about 75% (e.g. 60% to 90%) by weight of the cleansing article.

In one embodiment, the article of the instant invention includes one or more projections. In this context the term projections, also called protrusions, are clearly visible distinct masses of a particular shape that arise above the surface of the first body. The projections are characterized in part by an elevation which is defined as the distance from top of the projection to the surface of first body from which they emanate (see also below). In the cleansing articles of the invention, this elevation should be at least about 5 mm, preferably from about 5 mm to about 18 mm, and most preferably from about 5 mm to about 16 mm.

The projections are composed of a thermoplastic solid or semi-solid mass that is either water-soluble or water erodable (i.e., water dispersible under shear). This mass, called the mass of the projections, includes one or more surfactants that are suitable for cleansing the skin, a plasticizing agent, and various optional ingredients, as described below.

Surfactants are an essential component of the mass of the projections when present in a soap bar, as well as a component of the mass of the first body in the preferred embodiment of the invention. Surfactants make up from about 25% to about 90%, preferably about 50% to about 85% of the mass of the projections and the mass of the first body by weight in the preferred embodiment of the invention.

Useful and preferred surfactants for the present invention are fatty acid soaps, or simply soaps. The term "soap" is used herein in its popular sense, i.e., comprising the alkali metal or alkanol ammonium salts of aliphatic, alkane-, or alkene monocarboxylic acids. Sodium, potassium, magnesium, mono-, di- and tri-ethanol ammonium cations, or combinations thereof, are suitable for the purposes of this invention.

In general, sodium soaps are used in the compositions of this invention, but from about 1% to about 25% of the soap may be in the form of potassium and or magnesium soaps. The soaps useful herein are the well known alkali metal salts of natural of synthetic aliphatic (alkanoic or alkenoic) acids having about 8 to 22 carbon atoms, preferably about 8 to about 18 carbon atoms. They may be described as alkali metal carboxylates of hydrocarbons having about 8 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution similar to coconut oil or tallow, or mixtures thereof, since these are among the more readily available fats. The proportion of fatty acids having at least 12 carbon atoms in coconut oil soap is of about 85%. This proportion will be greater when mixtures of coconut oil and fats such as tallow, palm oil, or non-tropical nut oils or fats are used, wherein the main chain lengths are C16 and higher. Preferred soap for use in the compositions of this invention has at least about 85% of fatty acids having about 12 to 18 carbon atoms. However, soaps entirely of fatty acids derived from vegetable oils are also suitable.

Coconut oils employed for the soap may be substituted in whole or in part by other "high-lauric" oils, that is oils or fats wherein at least 50% of the total fatty acids is composed of lauric or myristic acids and mixtures thereof. These oils are generally exemplified by the tropical nut oils of the coconut oil class. For instance, they include palm kernel oil, babassu oil, ouricuri oil, tucum oil, cohune nut oil, murumuru oil, jaboty kernel oil, khakan kernel oil, dika nut oil, and ucuhuba butter.

A preferred soap is a mixture of about 10% to about 40% of lauric rich fatty acids (e.g., fatty acid mixtures relatively rich in lauric acid) such as those derived from coconut oil, palm kernal oil or babasu oil, and 90% to about 60% of high stearic soaps (relatively rich in stearic acid) such as those derived from tallow, palm stearin and palm oil.

The soaps may contain unsaturation in accordance with commercially acceptable standards. Excessive unsaturation is usually avoided.

Soaps may be made by the classic kettle boiling process or modern continuous soap manufacturing processes, wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C12), myristic (C14), palmitic (C16), or stearic (C18) acids with an alkali metal hydroxide or carbonate.

A second type of surfactant useful in the practice of this invention is a non-soap synthetic type detergent—a so-called syndet. Syndets can be of the anionic, zwitterionic, amphoteric or nonionic type, and well as mixtures of these types.

The anionic surfactant may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3, and M is a solubilizing cation such as sodium, potassium, ammonium or substituted ammonium. Ammonium and sodium lauryl ether sulfates are preferred.

The anionic surfactant may also be alkyl sulfosuccinates (including mono- and dialkyl, e.g., $C_6$-$C_{22}$ sulfosuccinates) alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, and acyl isethionates.

Sulfosuccinates may be monoalkyl sulfosuccinates having the formula:

$R^4O_2CCH_2CH(SO_3M)CO_2M$;

amido-MEA sulfosuccinates of the formula:

$R^4CONHCH_2CH_2O_2CCH_2CH(SO_3M)CO_2M$ wherein $R^4$ ranges from $C_8$-$C_{22}$ alkyl and M is a solubilizing cation; and amido-MIPA sulfosuccinates of formula:

$RCONH(CH_2)CH(CH_3)(SO_3M)CO_2M$ where M is as defined above.

Also included are the alkoxylated sulfosuccinates, wherein n=1 to 20; and M is as defined above.

Sarcosinates are generally indicated by the formula:

$RCON(CH_3)CH_2CO_2M$ wherein $R^2$ ranges from $C_8$ to $C_{20}$ alkyl and M is a solubilizing cation.

Taurates are generally identified by formula:

$R^2CONR^3CH_2CH_2SO_3M$ wherein $R^2$ ranges from $C_8$-$C_{20}$ alkyl, $R^3$ ranges from $C_1$-$C_4$ alkyl and M is a solubilizing cation.

Another class of anionics are carboxylates such as follows:

$R—(CH_2CH_2O)_nCO_2M$ wherein R is $C_8$ to $C_{20}$ alkyl; n is 0 to 20; and M is as defined above.

Another carboxylate which can be used is amido alkyl polypeptide carboxylates such as, for example, Monteine LCQ$^{(R)}$ by Seppic.

Another surfactant which may be used are the $C_8$-$C_{18}$ acyl isethionates. These esters are prepared by a reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5% to 15% by weight of the total composition. Preferably, this component is present in an amount from about 1% to about 10%.

The acyl isethionate may be an alkoxylated isethionate such as is described in Ilardi et al., U.S. Pat. No. 5,393,466, hereby incorporated by reference into the subject application.

Another surfactants that may be used are $C_8$ to $C_{22}$ neutralized fatty acids (soap). Preferably, the soap used has straight chain, saturated $C_{12}$ to $C_{18}$ neutralized fatty acids.

In general, the anionic component will comprise from about 1% to 20% by weight of the composition, preferably 2% to 15%, most preferably 5% to 12% by weight of the composition.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulphonate, sulfate, phosphate, or phosphonate. A general formula for these compounds is:

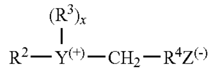

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulphonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-5-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

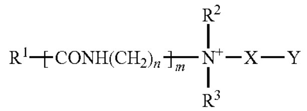

where $R^1$ is alkyl or alkenyl of 7 to 18 carbon atoms; $R^2$ and $R^3$ are each independently alkyl, hydroxyalkyl or carboxyalkyl of 1 to 3 carbon atoms; n is 2 to 4; m is 0 to 1; X is alkylene of 1 to 3 carbon atoms optionally substituted with hydroxyl, and Y is $—CO_2—$ or $—SO_3—$ Suitable amphoteric detergents within the above general formula include simple betaines of formula:

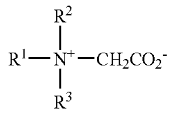

and amido betaines of formula:

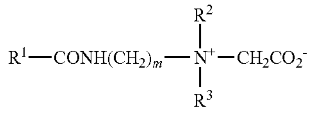

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

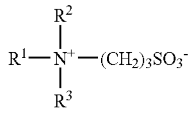

or

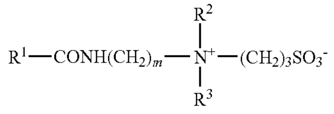

where m is 2 or 3, or variants of these in which $—(CH_2)_3SO^-_3$ is replaced by:

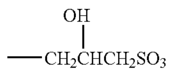

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic surfactant, when used, generally comprises 0.1% to 25%, preferably 1% to 20% by weight, more preferably 5% to 15% of the composition.

In addition to one or more anionic and optional amphoteric and/or zwitterionic surfactants, the surfactant system may optionally include a nonionic surfactant.

Although nonionic surfactants can be used in some embodiments, they are not preferred when the majority of the surfactant is soap. For such non-soap applications, nonionics that are the reaction products of compounds having a hydrophobic group and a reactive hydrogen atom, for example aliphatic alcohols, acids, amides or alkyl phenols with alkylene oxides, especially ethylene oxide either alone or with propylene oxide.

Specific suitable nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other suitable so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al., which is hereby incorporated by reference, or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula:

$$R^2O(C_nH_{2n}O)_t(glycosyl)_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Examples of suitable cationic detergents are the quaternary ammonium compounds such as alkyldimethylammonium halogenides.

Other surfactants which may be used are described in U.S. Pat. No. 3,723,325 to Parran Jr. and "Surface Active Agents and Detergents" (Vol. I & II) by Schwartz, Perry & Berch, both of which is also incorporated into the subject application by reference.

Although the surfactant may be a pure soap or a pure syndet, it is in some cases preferable to use a combination of soaps with synthetic detergents. Examples of combinations are disclosed in U.S. Pat. No. 4,695,395 to Caswell, et al.

A preferred embodiment of the invention is directed to articles that provide simultaneous massaging and cleansing of skin. Here, there are a multiplicity of projections that provide a massaging action. These projections must be of such a size so as to provide a distinctive sensory effect, but must also be sufficiently robust to withstand handling and misuse without fracturing, thus either separating said projections from the first body or exposing sharp edges.

The inventors have found that when the plasticity of the mass of the projections is in a certain range, the projections will resist fracture, while not being soft enough so as to deform during manufacture and distribution.

The inventors have further found that when the mass of the projections is principally composed of soap, a plasticizing agent is required to achieve the desired plasticity range, i.e., soap by itself is generally too brittle. For the purposes of this invention "plasticizing agent" is meant as a material that may alter the plastic index as measured in a controlled test, such as the 3-point bending test described below in the Evaluation Methodology Section.

Oils are particularly useful plasticizing agents in the current invention. One useful class of oils is ester oils; oils having at least one ester group in the molecule, especially fatty acid mono- and polyesters such as cetyl octanoate, octyl isonanoanate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester, sorbitol ester, and the like.

Triglycerides and modified triglycerides are also useful ester oils. These include vegetable oils such as palm kernel, jojoba, soybean, canola, sunflower, safflower, rice bran, avocado, almond, olive, sesame, persic, castor, coconut, and mink oils. These oils can also be hardened to remove unsaturation and alter their melting points. Synthetic triglycerides can also be. Some modified triglycerides include materials such as ethoxylated and maleated triglyceride derivatives.

Another type of ester oil is liquid polyester formed from the reaction of a dicarboxylic acid and a diol. An example such a polyester is marketed by ExxonMobil under the trade name PURESYN ESTER®.

A second class of plasticizing oils useful in the present invention include silicone and modified silicone oils. These oils include polydiorganosiloxanes such as polydimethylsiloxane (CTFA designation dimethicone), hydrocarbon modified silicone oils and waxes such as Dow Corning $KMSC_{30}$, polyether modified silicone oils such as Dow Corning DC 5200, and siloxanes having hydroxyl end groups (CTFA designation dimethiconol).

A third class of oils for use according to the present invention are hydrocarbon oils. These include linear and branched oils such as liquid paraffin, squalene, squalane, mineral oil, low viscosity synthetic hydrocarbons such as polyalphaolefin sold by ExxonMobil under the trade name of PureSyn PAO® and polybutene under the trade name PANALANE® or INDOPOL®. Highly branched hydrocarbon oils may also be suitable. Although more properly classified as grease, petrolatum can also potentially serve as a plasticizing agent if it is present in high enough amounts.

Some natural and synthetic waxes, although less preferred, can also be used as plasticers provided they have the correct melting point and solubility properties in the soap.

Another class of materials that can function as plasticizers are $C_8$-$C_{22}$ fatty acids, preferably $C_{12}$-$C_{18}$, preferably saturated, straight-chain fatty acids. However, some unsaturated fatty acids can also be employed. Of course the free fatty acids can be mixtures of shorter (e.g., $C_{10}$-$C_{14}$) and longer (e.g., $C_{16}$-$C_{18}$) chain fatty acids, although it is preferred that longer chain fatty acids predominate over the shorter chain fatty acids.

A particularly preferred fatty acid plasticizer is fatty acid derived from high lauric triglycerides such as coconut oil, palm kernel oil, and babasu oil.

The fatty acid can be incorporated directly, or be generated in-situ by the addition of protic acid. Examples of suitable protic acids include: HCl, adipic acid, citric acid, glycolic acid, acetic acid, formic acid, fumaric acid, lactic acid, malic acid, maleic acid, succinic acid, tartaric acid and polyacrylic acid. Other protic acids are mineral acids such as hydrochloric acids, phosphoric acid, sulfuric acid and the like.

Nonionic surfactants can also serve as plasticizers for the continuous phase. Nonionic surfactants in the context of instant invention are amphiphilic materials in which the polar groups are uncharged. Examples of suitable nonionic surfactants include ethoxylates (e.g. 6-25 moles ethylene oxide) of long chain (e.g. 12-22 carbon atoms) fatty alcohol (ether ethoxylates) and fatty acids; alkyl polyhydroxy amides such as alkyl glucamides; alkyl polyglycosides; esters of fatty acids with polyhydroxy compounds such as glycerol and sorbitol; ethoxylated mon-, di- and triglycerides, especially those having lower melting points; and fatty amides.

Other materials like nonionic surfactants as well as organic bases such as triethanolamine, although known to plasticize soap, are also much less preferred, and are preferably avoided for the present invention because of their effect in increasing the wear rate of the projections.

The level of plasticizing agent required depends upon the detailed composition of the mass of the projections. It has been found that the level of plasticizer should be such that the projection mass has a Plastic Index Measured by the Three Point Bending Test is in the range from about 7 mm to about 14 mm, preferably 7 mm to about 12 mm and most preferably from about 8 mm to about 11 mm. Inclusion of plasticizer(s) that achieves these ranges of plastic index provides projection bars of improved robustness relative to ordinary soap, i.e., the articles display a significantly lower frequency and extent of fracture in the Drop Test described in the methodology section.

It has been found that when the projections are predominantly composed of soap, the above plasticity range can be achieved by incorporating a plasticizer into the mass of the projections at a level from about 0.5% to about 15%, preferably from about 1% to about 10% and most preferably from about 1% to about 5% based on the total mass of the projections.

It has been surprisingly found that some plasticizing agents combined in the form of a plasticizing compound can function without affecting wear rate. Moreover, the inventors surprisingly found that some materials, especially when used in combination, thus forming a dual action plasticizing compound, can serve a dual role of achieving the required plasticity and simultaneously reducing the wear rate so as to increase the longevity of cleansing articles in use. Dual action compounds conceived under the scope of the present invention surprisingly and conveniently are shown to present technical effects contrary to what is know in the art available so far.

Specifically, while plasticizing agents widely used for, e.g. soap bars, do provide a desirable increase in the plasticity, on the other hand they usually provide at the same time the undesirable result of increasing the rate of wear. This is definitively undesirable when the article in case is a soap bar, and even more if the soap bar is provided with one or more projections arising out of one of its surfaces. In the latter case, the user is rapidly left with an ordinary soap after a few bathes.

These dual action plasticizing agents combined in the form of a dual action compound are preferred in the instant invention, especially in the case of the preferred embodiment where it is not only important that the protrusions be mechanically robust so as to resist fracture and excessive ductility (i.e., bending and indentation), but that they also not wear away too quickly in normal use.

The materials that potentially have this dual function appear to comprise combinations of oils that are liquid, water insoluble and weakly polar or weakly amphiphilic. Without wishing to be bound by theory, it is believed that these materials when in the form of a dual action compound can coat microscopic regions or domains in the soap mass, and reduce their erosion during use. Materials useful for the said compound include ester oils, especially fatty acid monoesters such as isopropyl myristate and palmitate; high lauric fatty acids such as coconut oil or palm kernel oil fatty acid and silicone oils, especially polydimethyl siloxane (dimethicone) having a viscosity between about 4,000 and about 10,000 cst; and mixtures thereof.

An especially preferred dual action plasticizing compound for the instant invention is a mixture of isopropyl myristate, palm kernel oil fatty acid, and polydimethylsiloxane (dimethicone).

A variety of optional ingredients can be incorporated in either the first body or the projections. However, these optional materials can impact the plasticity and wear-rate of the projects and the manufacturability of the cleansing article, and this must be borne in mind in selecting such materials and the appropriate tests carried out. Potential optional materials are described below.

It is sometimes beneficial to include hardening agents in the mass of the projections, as well as the mass of the first body when the latter is a water soluble/water dispersible thermoplastic.

Polyols and inorganic electrolytes are useful hardening agents for compositions based on fatty acid soaps. Polyols are defined here as molecules having multiple hydroxyl groups. Preferred polyols include glycerol, propylene glycol, sorbitol, and polyvinyl alcohol.

Preferred inorganic electrolytes include monovalent chloride salts, especially sodium chloride; monovalent and divalent sulfate salts like sodium sulfate; sodium carbonate; monovalent aluminate salts, monovalent phosphates, phosphonates, polyphosphate salts; and mixtures thereof. Further, the composition may include a crystalline or amorphous alumminum hydroxide that can be generated in-situ by reacting fatty acids and/or non-fatty mono- or polycarboxylic acids with sodium aluminate, or can be prepared separately by reacting fatty acids and/or non-fatty mono- or polycarboxylic acids with sodium aluminate and adding the reaction product to the soap.

In addition to the ingredients described above, the compositions of the masses of the cleansing article can also contain a variety of optional ingredients used to increase shelf life, aesthetics or functionality. The ingredients can be found in one or both of the constituent masses. Such adjuvants include chelating agents such as EDTA, preservatives like dimethyloldimethylhydantoin (Glydant XL1000), parabens, sorbic acid antioxidants such as, for example, butylated hydroxytoluene (BHT); various natural and synthetic perfume components; colorants such as Acid Blue 9, Acid Green 25, Food Yellow 13, and Food Red 1 and mixtures thereof, and the like.

Particularly useful optional ingredients are skin benefit agents used to deliver some useful end benefit to the skin, and optical modifiers used to confer a unique appearance to the bar. However, the caveat already made about plasticity, wear-rate and manufacturability must be again mentioned.

The first class of ingredients includes nutrients used to moisturize and strengthen the skin with. These include:

a) vitamins such as vitamin A and E, and vitamin alkyl esters such as vitamin C alkyl esters;
b) lipids such as cholesterol, cholesterol esters, lanolin ceramides, sucrose esters, and pseudo-ceramides;
c) liposome-forming materials such as phospholipids, and suitable amphiphilic molecules having two long hydrocarbon chains;
d) essential fatty acids, poly-unsaturated fatty acids, and sources of these materials;
e) triglycerides of unsaturated fatty acids such as sunflower oil, primrose oil, avocado oil, almond oil;
f) vegetable butters formed from mixtures of saturated and unsaturated fatty acids such as shea butter; and
g) minerals such as sources of zinc, magnesium, and iron;

A second type of skin benefit agent is a skin conditioner used to provide a moisturized feel to the skin. Suitable skin conditioners include:

a) silicone oils, gums and modifications thereof such as linear and cyclic polydimethylsiloxanes, amino, alkyl, and alkylaryl silicone oils;
b) hydrocarbons such as liquid paraffin, petrolatum, microcrystalline wax, ceresin, squalene, pristan, paraffin wax and mineral oil;
c) conditioning proteins such as milk proteins, silk proteins and glutins;
d) cationic polymers as conditioners which may be sued include Quatrisoft LM-200 Polyquaternium-24, Merquat Plus 3330-Polyquaternium 39; and Jaguar® type conditioners;
e) humectants such as glycerol, sorbitol, and urea; and
f) emollients such as esters of long chain fatty acids, such as isopropyl palmitate and cetyl lactate;

A third type of benefit includes deep cleansing agents. These are defined here as ingredients that can either increase the sense of refreshment immediately after cleansing, or can provide a sustained effect on skin problems that are associated with incomplete cleansing. Deep cleansing agents include:

a) antimicrobials such as 2-hydroxy-4,2', 4'-trichlorodiphenylether (DP300), 2,6-dimethyl-4-hydroxychlorobenzene (PCMX), 3,4,4'-trichlorocarbanilide (TCC), 3-trifluoromethyl-4,4'-dichlorocarbanilide (TFC), benzoyl peroxide, zinc sales, tea tree oil;
b) anti-acne agents, such as salicylic acid, lactic acid, glycolic acid, and citric acid, and benzoyl peroxide (also an antimicrobial agent);
c) oil control agents including sebum suppressants, mattifiers such as silica, titanium dioxide, oil absorbers such as microsponges;
d) astringents including tannins, zinc and aluminum salts, plant extracts such as from green tea and Witchhazel (Hammailes);
e) scrub and exfolliating particles, such as polyethylene spheres, agglomerated silica, sodium bentonite granules, sugar, ground pits, seeds, and husks such as from walnuts, peach, avacado, and oats, sales;
f) cooling agents such as methol and its various derivatives and lower alcohols;
g) fruit and herbal extracts;
h) skin calming agents such as aloe vera; and
i) essential oils such as menth, jasmine, camphor, white cedar, bitter orange peel, ryu, turpentine, cinnamon, bergamot, citrus unsiu, calamus, pine lavendar, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, penene, limonene and terpenoid oils.

Other benefit agents that can be employed include antiageing compounds sunscreens, and skin lightening agents.

When the benefit agent is oil, especially low viscosity oil, it may be advantageous to pre-thicken it to enhance its delivery. In such cases, hydrophobic polymers of the type described in U.S. Pat. No. 5,817,609 to He et al may be employed, which is incorporated by reference into the subject application.

The benefit agent generally comprises 0 to about 25% by wt. of the total composition, of the projections and/or the first body, preferably about 0.25% to about 10%, and most preferably between about 0.25% to about 5% by weight.

Emotive ingredients that enhance the perception of massaging action and skin care are also useful. Examples include grape seed oil, Ylang Ylang, proteins such as collagen and elastin, agar agar and other hydrocolloids, liposomes, seaweed, caffeine, retinol, pineapple extract, almond oil, sandalwood oil and vitamin E.

A final group of optional ingredients includes optical modifiers which are defined as materials that modify the optical texture or transparency of each component of the cleansing article, or introduce a pattern to increase the distinctiveness of one or both of the components. Examples of suitable optical modifiers include:

a) speckles/bits such as ground fruit pits, seeds, polyethylene beads, mineral agglomerates, loofha, and sodium bentonite;

b) reflective plate-like particles such as mica;

c) pearlizing agents such as coated micas, and certain waxes;

d) wax/plastic slivers that resemble for example fruits slices;

e) Vegetable or fruit slivers;

f) Transparency enhancing additives, especially those that do not affect wear-rate;

g) mattefiers such as $TiO_2$; and h) mixtures of the above.

Further, either component mass can be made multi-colored, e.g., striped, through the judicious use of dye, as is well known in the art.

The geometrical specification of cleansing articles of the invention can be described by various geometric parameters that relate to the shape, number and dimensions of the protrusions and the shape and dimensions of the first body. With reference to FIG. 1, these parameters are defined below.

FIG. 1 shows a schematic diagram of a cleansing article with projections. The first body FB is characterized by the shape of the surface FS from which the projection(s) P emanate. In this case the face FS has rectangular aspect with curved long sides (but it could also comprise a variety of shapes), and has a minor axis of average length X, and a major axis of average length Y. The face of the first body FS is also characterized by an average total surface area. The first body FB is also characterized by an average thickness Z.

The projections are schematically represented by P1 and P2 in FIG. 1. For purposes of illustration, there are two types of projections. Projections P1 have the shape of a right circular cylinder, while projections P2 have an elliptical cross section in this case. However, in practice the projections can have a variety of shapes. The projections P1 and P2 are characterized by a terminal surface TS1 and TS2 defined as the surface of the projection furthest removed from the surface of the first body from which they emanate. The elevation E (in this case both types of projections have the same elevation) is defined as the average distance from the terminal surface TS to the surface plan FS of the first body FB.

The geometric properties used to characterize the cleansing articles of the invention are summarized below:

First Body
- Overall Shape
- Average dimensions

Projections
- Average shape(s)
- Total number of each type per article
- Dimensions of terminal surface
- Elevation(s) of terminal surface(s) above surface of first body A variety of articles are exemplified schematically in FIG. 2. FIG. 2A and FIG. 2B illustrate hemispherical and hemi elliptical projections respectively. FIG. 2C illustrates multiple projections of triangular and rectangular cross section. FIG. 2D illustrates cylindrical projections having different cross sections. FIG. 2E and FIG. 2F illustrate projection bars having a multiplicity of hemispherical projections. FIG. 2G illustrates a combination of elliptical and circular cylindrical projections. In the examples shown in FIG. 2, the projects emanate for a single surface of the first body. However this need not be the case, and indeed different types of projections can be on each surface of the article, e.g., multiplicity of protrusions on one surface, and single embossed projection on the opposite surface.

Test Methodology

Cylinder Impaction Test for Hardness

When it is desired to fabricate the article as a projection bar as defined above, it is useful to measure the hardness of the masses of the first body and of the projections. Such a measurement can provide a good indication of whether a projection bar can be fabricated from such masses, e.g., by high speed extrusion and finishing.

A variety of methods are known in the art to measure the hardness of soft solids used to fabricate toilet bars. The most common techniques are the Cylinder Impaction Test which measures the maximum force before yielding, and the Penetration Test which measures the penetration of a needle under a constant load. Although the invention is described by parameters that are measured by the Cylinder Impaction Test, this was done for convenience from a manufacturing perspective. The various hardness tests can obviously be inter-correlated.

The Cylinder Impaction Test employs a modified Crush-Test protocol that is used for measuring carton strength. A Regmed Crush Tester was employed.

Samples (typically 8×5×2 cm) at the desired temperature were placed on the lower plate of the tester fitted with a pressure gauge and a temperature probe inserted in the sample, approximately 4 cm from the test area. An 89 gm inox metallic cylinder (2.2 cm in diameter (0.784 in) and 3 cm in length (1.18 in)) was placed at a central location on the top of the sample. The upper plate was then lowered to just touch the cylinder.

The top plate was then lowered at a programmed rate of 0.635±0.13 mm/s (0.025±0.005 in/sec). At a certain strain, the sample will yield, bend or fracture, and the maximum force expressed as PSI (lbs/inch$^2$) and average sample temperatures are recorded. The water content of the sample was measured immediately after the test by microwave analysis.

The hardness measurement was repeated a total of 3 times with fresh samples, and the results were considered on their average values. It is important to control the temperature and water content of the sample, since hardness is sensitive to both these variables.

Penetration Test

A model PNR10 penetrometer manufactured by FUR Berlin was employed. Three standard cones (needles) were used; 2.5 g (18-0063), diameter: 0.9-3.05 mm, length: 79 mm and the measurements were carried out as follows.

The cone is moved nearer to the surface of the test mass at the desired temperature with the coarse cone adjustment knob, and then moved to just touch the surface of the test material with the fine cone adjustment knob. The start button is then pressed, releasing the cone weighing 100 g for a time period of 60 sec., at which time the penetration distance that the cone travels in the sample is measured and shown on a displacement gauge display. The reset button is pressed, and the cone is lifted back to its zero position.

Three-Point Bending Test of Plasticity

The plasticity was measured using a Three-Point Bend Test. A Stable Micro System—TA-XT Plus—Texture Analyser from Braseq—Brasileira de Equipamentos Ltda. fitted with a three-point bend rig attachment was used to obtain force and displacement data. The three-point bend test rig consisted of a 5×40 mm rectangular indenter and two static 10×40 mm rectangular supports which were separated by a distance of 48 mm.

A billet or bar made of the projection mass (70 mm long with a square cross section of 38×38 mm) was prepared by extrusion and wrapped in plastic and equilibrated at 25° C. for three days. After equilibration the sample was placed on the rectangular supports. After equilibration to room temperature (25° C.) the indenter was brought to the surface of the bar. The force was then measured as a function of displacement of the indenter at a displacement rate of 1 mm/sec. This was continued until the bar fractured, which was signalled by an abrupt drop in force. The maximum displacement in millimeters at fracture was used as the "Plastic Index" of the protrusion composition tested. Each experiment was repeated a total of 9 times, and the average Plastic Index was calculated and used for comparison of different compositions.

It is desirable that the plastic radius is in the range from about 6.5 mm to about 15 mm, preferably 6.5 mm to about 14 mm and most preferably from about 6.5 mm to about 12 mm.

Intrinsic Wear Rate—Controlled Rubbing Test

The Intrinsic Wear Rate of the mass of the protrusions is measured by the following procedure.

This test, which provides data on the weight loss of a thermoplastic soap mass as a result of a controlled wash down procedure, is defined as its intrinsic wear rate.

The mass is molded into uniform shaped tablets which are washed down at intervals, under controlled conditions, over a period of 4 days. After drying out the weight loss from each sample is determined.

Tablets 7.5 cm long×5.5 cm wide×2.3 cm thick are washed down in a controlled manner, 6 times per day for 4 days. The tablets are stored in controlled conditions after each wash down, and the weight loss is determined after a further 2 or 3 days drying out.

Four soap tablets of each composition are weighed and put on coded soap trays. A wash bowl is filled with water (5 liters) at 25° C. Wearing waterproof gloves, the tablets are immersed in the water, and twisted 15 times (through 180° each time) in the hands above the water. This procedure is then repeated for a total of 30 rubs. The tablet is then immersed in the water again, to wash off the lather, and then placed back on its soap tray, ensuring that the opposite face is uppermost.

For each composition this full wash down procedure is carried 6 times per day for 4 consecutive days, at evenly spaced intervals during each day. Alternate the face placed down after each wash down. Between wash downs the soap trays are left on an open bench or draining board, in ambient conditions. After each wash down cycle, change the position of each soap tray/tablet, to minimize variability in drying conditions. At the end of each day each soap tray with drainer is rinsed and dried.

The Intrinsic Wear Rate is defined as the weight lost in percentage, i.e., Intrinsic Wear Rate=(initial weight−final weight)×100/initial weight.

Drop Test

This test measures the impact resistance of a projection bar, and is used to quantify the resilience of the bar during in store handling or accidental dropping during use.

Each projection bar is first examined for overall integrity looking for cracks, or existing damage before doing the trial. Any low quality sample is rejected to avoid interference. The test bar (unwrapped) is place in the desired landing position on an adjustable platform whose height above the impact surface is adjusted to 1.80 meters. A Lansmont model PDT-56 drop platform was employed. The impact surface was a steel plate which was level, smooth, dry and rust-free. The test bar was centered in the middle of the parting line of the platform.

The bar was then dropped, ensuring that it landed in the same position as it was placed on the platform. After the drop, any failure was noted, and the bars were rated according to the criteria given below. Photographs were also taken to document the outcome.

For each composition a total of 30 projection bars were tested under the following three geometric impact conditions (10 samples each):

Upright position—lying down on the minor axis side. The base of the sample will land evenly flat on the impact surface;

Upright in 45° angle sideways position—laying down on the minor axis edge. The corner of the sample will land flat on the impact surface.

Upright in 45° angle front position—laying down on the medium axis edge. The edge corner of the sample will land flat on the impact surface.

The grading scale is defined in the table below.

Drop Test Grade for Projection Bars

| Drop Test Score | Description |
|---|---|
| 1 | Crushing with or without light fissures - small fissures that will not turn into pieces. |
| 2 | Crushing with medium size fissures - medium fissures that will not turn into pieces. |
| 3 | Crushing with heavy fissures - Heavy fissures that will not turn into pieces. |
| 4 | Breakage apart - breakage into piece or pieces up to 15% of the amount of samples and maximum 1 protrusion breakage per individual sample. |
| 5 | Breakage apart - breakage into piece or pieces in more than 15% of the amount of samples or more than 1 protrusion per individual sample. |

Article Manufacture

Projection bars, such as soap bars, can be of two broad types; first body and projections are made with the same mass, or the two components are made with different masses.

First Body and Projection Mass with the Same Composition

When the mass is predominantly composed of soap, the article can be made in a standard toilet soaps finishing line with some modification in stamping and wrapping using processing techniques and equipment well known in the art.

The first step of this process involves the mixing of mass from storage silos with desired plasticizing agents, optionally hardening agents and other ingredients in a batch mixer. The objective of this operation is to generate a good distribution of the ingredients throughout the bulk of the mass.

After mixing, the mass is generally passed through a refiner followed by a roll mill to achieve micro-mixing and improve composition uniformity.

Finally, the mass will be further refined and plodded, usually under vacuum, in a two-stage operation with a single or twin worm conFig.uration with an intermediate vacuum chamber, compacted into a coherent mass and extruded as a bar or billet for cutting and stamping. Both the final refiner and plodder stages play a part in completing the total mixing process by providing additional micro-mixing. Solid ingredients, dyes and different colored soap can be added during the final billet making by processes known in the art, e.g., dye injection through pressure plates.

If done under vacuum, this vacuum is typically applied during mixing and refining, until the combined masses are extruded through, for example, a nosecone. Typically, the vacuum is at 500 to 600 mm pressure (measured as mercury or Hg pressure).

The billets are then cut into bars that are then molded into the desired projection bar shape by stamping using a clam shell capacity mold.

First Body and Projection Mass with Different Compositions

Projection bars of this type can be prepared for example by co-extrusion processes. Co-extrusion of toilet bars is known in the art and is described for example in WO 01/91990, U.S. Pat. Nos. 4,459,094, 3,884,605, and 4,634,564 and references therein.

One route utilizes two extruders that feed the two different masses into a split nosecone coupled to a "split eye plate". Alternatively, the two compositions can be fed to the split nosecone via a non-communicating twin-screw extruders, wherein each screw is fed separately.

The split eye plate may be corrugated at the junction point of the two parts of the billet to increase the mechanical strength of the junction, as described in U.S. Pat. No. 5,198,140. One or both compositions may also incorporate ingredient(s) that increase(s) adhesion of the two compositions.

The co-extrusion process outlined above yields a billet that is split longitudinally into two parts of different composition; one composition corresponding to the projections, and the other to the first body. The volume ratio of each material corresponds to the volume ratio for the component of the projection bar.

After the two part billet is formed, it is cut and oriented so that each mass matches the corresponding direction for entry into a mold or die, so that it can be properly stamped.

First Body and Projection Mass with Different ConFig.urations

Many are, in fact, the possibilities to define a conFig.uration for the articles of the present invention.

In one possible embodiment, the thickness of the first body portion would be greater than the height of the projections measured from the base to the highest point on the projection.

Of course, in other embodiments the height of the projection can be higher than the thickness of the base.

Another alternative conFig.uration would be providing the first body portion with a substantially parallepipedal shape and one or more protrusions arising out of one of the surfaces of same.

In one of such cases, the height of said protrusions can be from about 46% to about 50% of the total thickness of said bar soap, presenting a height of said protrusions from about mm to about 20 mm, preferably from 12 mm to about 15 mm.

EXAMPLES

The following examples are intended to further illustrate the invention, and are not intended to limit the invention in any way. All percentages used, unless indicated otherwise, are intended to be percentages by weight.

Examples 1-5 illustrate articles in which the composition of the surfactant mass of the first body is identical with the surfactant mass of the projections. These articles have geometrical characteristics that are very useful as massaging cleansing bars, and some are highly appreciated by consumers for their robustness, economy and in-use sensory properties.

Example 1

Influence of Plasticity on Fracture Resistance

This example illustrates the criticality of plasticizer on the resistance to fracture of soap bars having a multiplicity of protrusions. The soap masses whose compositions are given in Table 1A were prepared by the extrusions process described in the Bar Manufacture Section at a 5 kg scale using a 100 mm plodder. Each composition was hand stamped in mold that produced an article having the geometric properties described in Table 1B and shown schematically in FIG. 1. Thus, in this example the composition of the surfactant mass of the first body and of the projections is the same.

The plasticity of the compositions as measured by the Degree of Deformation in the Three Point Bending Test and their degree of fracture as measured by the Drop Test Score are also recorded in Table 1A.

Soap masses that were sufficiently plastic to exhibit a Degree of Deformation greater than about 7 mm also exhibited minimal fracture of the protrusions in the Drop Test, which is used to estimate the resilience of the article to handling at point of purchase and in-use by consumers.

TABLE 1A

| Compositions of soap masses used in Example 1 | | | | | |
|---|---|---|---|---|---|
| INGREDIENT | C 1 | Ex. 1A | Ex. 1B<br>WEIGHT % | Ex. 1C | Ex. 1D |
| SURFACTANTS | | | | | |
| Anhydrous Sodium Soap (85Tallow/15PKO) | TO 100% | TO 100% | TO 100% | TO 100% | TO 100% |
| PLASTICIZING AGENTS | | | | | |
| Isopropyl Myristate | 0 | 0 | 0.5 | 0 | 0.5 |
| Dimethicone (Polidimetylsiloxane 5000 cs) | 0 | 2.0 | 0 | 0 | 0.5 |
| Palm kernel oil FA | 0 | 0 | 0.5 | 0 | 0.5 |
| Sunflower seed oil | 0 | 2.0 | 0 | 0 | 0 |
| Petrolatum | 0 | 0 | 0 | 0.4 | 0 |
| MINORS (Glycerol, perfume, colorant, antioxidant, pigment, exfoliating, seed oil/extract, agar agar, sodium chloride, citric acid) | 5.63077 | 4.87217 | 3.05217 | 6.44077 | 3.15217 |
| WATER | 13.5 | 13.5 | 13.5 | 13.5 | 13.5 |
| EVALUATIONS | | | | | |
| Degree of bending, mm | 4.6 | 7 | 11.4 | 6.6 | 10.3 |
| Drop Test evaluation | 4.2 | 3.3 | 1.3 | 4.3 | 2.1 |
| Robust in Use | No | Yes | Yes | No | Yes |

TABLE 1B

| Geometric characteristics of Example 1 articles (C 1 and Ex. 1A-Ex. 1D) | |
|---|---|
| GEOMETRIC CHARACTERISTICS | Value |
| Dimensions of first body (L × W × H), cm | 9.4 cm × 6.4 cm × 1.6 cm |
| Geometry of projections | Circular and elliptical cylinders |
| Number of projections | 7 elliptical cylinders<br>6 circular cylinders |
| Height of terminal surface above first body, cm | 1.35 cm |
| Terminal surface area of projection, $cm^2$ | Circular 1.13 $cm^2$<br>Elliptical 1.78 $cm^2$ |

Example 2

Influence of Composition on Plasticity and Wear Rate

This example illustrates the required plasticity and objective wear rate to achieve acceptable robustness and economy in use. A series of articles of identical geometry were prepared by the methods of Example 1. The geometrical properties were the same as that used in Example 1, and given in Table 1B. The compositions are given in Table 2A, and their pertinent physical properties are summarized in Table 2B.

Two points are noteworthy from Table 2B. First, it is seen that the projection mass should have an objective wear rate of less than about 31 for acceptable wear in use.

Comparing samples C 2A and Ex. 2C, it is seen that a relatively small change in composition can lead to a very significant change in properties such as wear rate, which make the difference between a bar that is acceptable to consumers (Ex. 2C), and one that is not (C 2A).

TABLE 2A

| Compositions used in Example 2 | | | | | |
|---|---|---|---|---|---|
| INGREDIENT | C 2A | C 2B | Ex. 2A<br>WEIGHT % | Ex. 2B | Ex. 2C |
| SURFACTANTS | | | | | |
| Anhydrous Sodium Soap (85 Tallow/15 PKO) | TO 100% | TO 100% | TO 100% | TO 100% | TO 100% |
| PLASTICIZING AGENTS | | | | | |
| Isopropyl Myristate | 0.5 | 0 | 3.0 | 5.0 | 0.5 |
| Dimethicone (polydimethylsiloxane 5000 cst) | 0 | 0 | 0 | 0 | 0.5 |
| Palm kernel oil FA | 0.5 | 1.25 | 0.5 | 0.5 | 0.5 |

TABLE 2A-continued

| Compositions used in Example 2 | | | | | |
|---|---|---|---|---|---|
| | C 2A | C 2B | Ex. 2A | Ex. 2B | Ex. 2C |
| INGREDIENT | | | WEIGHT % | | |
| OTHERS (glycerol, propylene glycol, TEA, sorbitol, perfume, colorant, antioxidant, pigment, exfoliating, seed oil/extract, agar agar, sodium chloride) | 3.05217 | 16.51395 | 3.05217 | 3.05217 | 3.15217 |
| WATER | 13.5 | 13.5 | 13.5 | 13.5 | 13.5 |

TABLE 2B

| Evaluation of samples used in Example 2 | | | | | |
|---|---|---|---|---|---|
| EVALUATIONS | C 2A | C 2B | Ex. 2A | Ex. 2B | Ex. 2C |
| Degree of bending (mm) | 11.4 | 17.4 | 15.1 | 16.3 | 10.3 |
| Objective Wear Rate (%) | 31.4 | 35.5 | 24.3 | 26.27 | 29.6 |
| Robustness Comments | Acceptable Projections wear away quickly | Acceptable Projections wear away quickly | Acceptable Projections have acceptable wear rate | Acceptable Projections have acceptable wear rate | Acceptable Projections have acceptable wear rate |

Example 3

Effect of Wear Rate on Yield

This example further illustrates the effect of objective wear rate on the yield of articles having a geometrical format as given in Table 1B, and being suitable as massage bars. The articles whose compositions are given in Table 3A were prepared by the procedure used in Example 1. The Objective Wear Rates and Yields were measured as set for in the METHODOLOGY SECTION. The results are shown in Table 3B.

The results support the conclusions drawn in Example 2, namely that the compositions should have an Intrinsic Wear Rate which is less than about 33%, preferably less than about 31% for an article with this general geometrical conFig.uration to make the protrusions last sufficiently long.

TABLE 3A

| Compositions used in Example 3 | | | | | | |
|---|---|---|---|---|---|---|
| | C 3A | C 3B | C 3C | Ex. 3A | Ex. 3B | Ex. 3C |
| INGREDIENT | | | | WT % | | |
| SURFACTANTS | | | | | | |
| Anhydrous Sodium Soap (90Tallow/10PKO) | TO 100% | TO 100% | | | | |
| Anhydrous Sodium Soap (85Tallow/15PKO) | | | TO 100% | TO 100% | TO 100% | TO 100% |
| PLASTICIZING AGENTS | | | | | | |
| Isopropyl Myristate | 0 | 0 | 0 | 0 | 3.0 | 0.5 |
| Dimethicone (5000 cst) | 0 | 0 | 0 | 0 | 0 | 0.5 |
| Palm kernel oil FA | 0 | 0 | 0.16 | 0 | 0.5 | 0.5 |
| Sunflower seed oil | 0.4 | 0.5 | 1.6 | 0 | 0 | 0 |
| Petrolatum | 0 | 0 | 0 | 0.4 | 0 | 0 |
| Glycerol | 2.0 | 0.18 | 2.6 | 3.0 | 0.18 | 0.18 |
| PEG | 0 | 0 | 0.3 | 0 | 0 | 0 |
| Sorbitol | 0 | 0 | 0 | 0 | 0 | 0 |
| TEA | 0 | 0 | 0.3 | 0 | | |
| Calcium Carbonate | 0 | 10.0 | 0 | 0 | 0 | 0 |
| OTHERS (perfume, colorant, antioxidant, pigment, exfoliating, seed oil/extract, agar agar, sodium chloride, sodium carbonate) | 2.88 | 2.364 | 2.97217 | 1.69217 | 2.87217 | 2.87217 |
| WATER | 14.5 | 13.5 | 13.2 | 13.5 | 13.5 | 13.5 |

TABLE 3B

| Evaluation of samples used in Example 2 | | | | | | |
|---|---|---|---|---|---|---|
| EVALUATIONS | C 3A | C 3B | C 3C | Ex. $3^A$ | Ex. 3B | Ex. 3C |
| Objective Wear Rate (Brick Shape Intrinsic) % | 34.5 | 43 | 39.5 | 33.74 | 24.3 | 29.6 |
| Comments | Projections wear away too quickly | Projections wear away too quickly | Projections wear away too quickly | Projections marginally acceptable wear rate | Projections have acceptable wear rate | Projections have acceptable wear rate |

Example 4

Requirements for High-speed Manufacture

Although compositions with the correct plasticity and wear rate are both robust and economical, not all of these compositions, as discussed above are suitable for high speed manufacture. Some compositions are too soft at extrusion processing temperatures, typically between about 38° C. and about 42° C. Other compositions are too pliable or too sticky at lower temperatures for high speed automated stamping and/or wrapping. This example illustrates the relevant criticalities.

Articles having the compositions set forth in Table 4A and all having the same geometrical characteristics as in Table 1B were prepared were prepared by the methods of Example 1.

The samples were evaluated for Hardness at 32° C.-42° C. by the Cylinder Impaction Test (lower temperatures were used because of excessive softening), and for Plastic Index at 25° C. by the Three-Point Bending Test. Some sample compositions were not extrudable even at the pilot scale used in Example 1. Samples that were extrudable were further evaluated in continuous (automated) stamping equipment, and wrapping machines. The results are shown in Table 4B.

TABLE 4A

| Compositions used in Example 4 | | | | | | |
|---|---|---|---|---|---|---|
| | C 4A | C 4B | C 4C | C 4D | Ex. 4A | Ex. 4B |
| INGREDIENT | Weight % | | | | | |
| SURFACTANTS | | | | | | |
| Sodium Soap | 33 | 0 | 0 | 0 | 0 | 0 |
| SLS | 7.0 | 0 | 0 | 0 | 0 | 0 |
| Anhydrous Sodium Soap (85 Tallow/15 PKO) | 0 | TO 100% | TO 100% | TO 100% | TO 100% | TO 100% |
| PLASTICIZING AGENTS | | | | | | |
| Isopropyl Palmitate | 0 | 0 | 0 | 0 | 2.0 | 0 |
| Isopropyl Myristate | 0 | 5.0 | 0 | 3.0 | 0 | 0.5 |
| Dimethicone – polydimethylsiloxane 5000 cs | 0 | 0 | | 0 | 0 | 0.5 |
| Blend Dimethicone + Alkyl Methyl Siloxane + Alkyl Methyl Siloxane Copolyol | 0 | 0 | 10 | 0 | 0 | 0 |
| Palm kernel oil FA | 0 | 0.5 | 0 | 0.5 | 0.5 | 0.5 |
| EMOLIENT/SOLVENT | | | | | | |
| Glycerol | 0 | 0.18 | 0.18 | 0.18 | 0.18 | 0.18 |
| Propylene Glycol | 8.0 | 0 | 0 | 0 | 0 | 0 |
| Isopropyl Alcohol | 2.5 | 0 | 0 | 0 | 0 | 0 |
| PEG | 5.00 | 0 | 0 | 0 | 0 | 0 |
| Sorbitol | 17.5 | 0 | 0 | 0 | 0 | 0 |
| MINORS (perfume, colorant, antioxidant, pigments, exfoliating) | 2.6 | 2.04217 | 2.04217 | 2.04217 | 2.04217 | 2.04217 |
| WATER | TO 100% | 13.5 | 13.5 | 13.5 | 13.5 | 13.5 |

TABLE 4B

| Evaluation of samples used in Example 4 | | | | | | |
|---|---|---|---|---|---|---|
| EVALUATIONS | C 4A | C 4B | C 4C | C 4D | Ex. 4A | Ex. 4B |
| Plasticity 23° C. mm | — | 16.322 | — | 15.136 | — | 10.289 |
| Cylinder Impaction Test $Lbs/in^2$ | 2 $lbs/in^2$ 48° C. (P. Plant) | 14 $lbs/in^2$ 32° C. (P. Plant) | 20 $lbs/in^2$ 32° C. (P. Plant) | 20 $lbs/in^2$ 33.4° C. (P. Plant) | 24 $lbs/in^2$ 38° C. (P. Plant) | 28 $lbs/in^2$ 40.9° C. (Main Plat) |
| Extrusion Evaluation | Too soft to extrude-liquefies in plodder | Too soft to extrude Properly Churns in plodder | | | Acceptable at 50 bars per minute | Acceptable at 100 bars per minute |
| Stamping Evaluation | | Sticks to mold - protrusions irregular and not uniform | Sticks to mold - protrusions irregular and not uniform | Demolds cleanly - Irregular protrusions | Demolds cleanly - uniform protrusions sharply defined | Demolds cleanly - uniform protrusions sharply defined |
| Packing Evaluation | | Deforms during wrapping | Deforms during wrapping | Protrusions deform during wrapping | Protrusions deform during wrapping | Can be wrapped or cartoned |

Examples Ex. 4A and Ex. 4B, whose compositions exhibited Hardness Values and Pliability Index in the range in which the inventors have found suitable for automated manufacture, could indeed be extruded, stamped and wrapped in automated equipment at a minimum production rate of 50 bars per minute.

Example 5

Articles with Various Geometrical Forms

Examples Ex. 5A-Ex. 5D illustrate various articles having the different geometrical characteristics as identified in Table 5. Here the first body in comprised of a surfactant mass that is substantially the same as the surfactant mass of the projections. The composition of the surfactant mass is either the composition of Ex. 4A or 4B. These articles are designed for personal cleansing and have plasticity, penetration value and wear rate in the optimum for robust, economical projection bars that are capable of being produced by efficient high-speed manufacture.

Figure 2A:
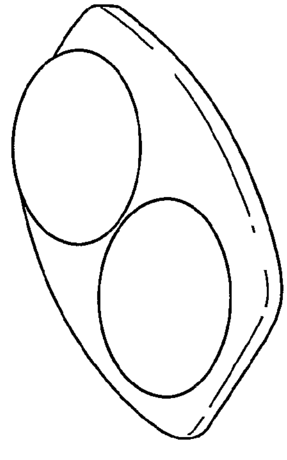
FIG. 2A is a perspective view of a first embodiment of a projection bar of the invention.
Figure 2B:
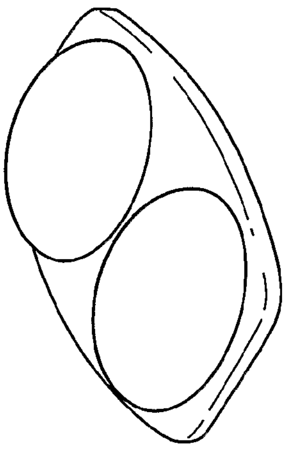
FIG. 2B is a perspective view of a second embodiment of a projection bar of the invention.

Ex. 5A and Ex. 5B have spherical and elliptical shaped projections as shown schematically in FIG. 2A and FIG. 2B respectively.

Figure 2C:
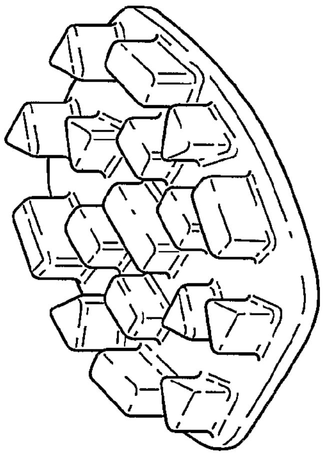
FIG. 2C is a perspective view of a third embodiment of a projection bar of the invention.

Ex. 5C has a mixture of long and short rectangular and triangular shaped projections as shown schematically in FIG. 2C.

Figure 2D:
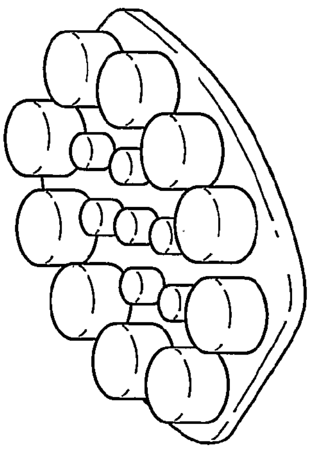
FIG. 2D is a perspective view of a fourth embodiment of a projection bar of the invention.

Ex. 5D has a multiplicity of circular cylindrical shaped projections of different diameters as shown schematically in FIG. 2D.

Figure 2E:
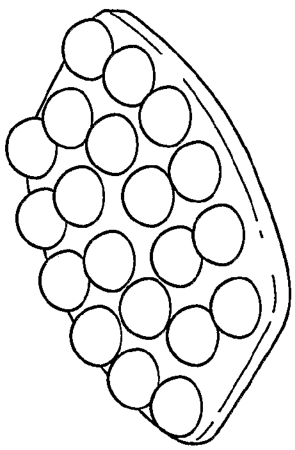
FIG. 2E is a perspective view of a fifth embodiment of a projection bar of the invention.

Ex. 5E has a multiplicity of hemispherical projection as shown schematically in FIG. 2E.

Figure 2F:
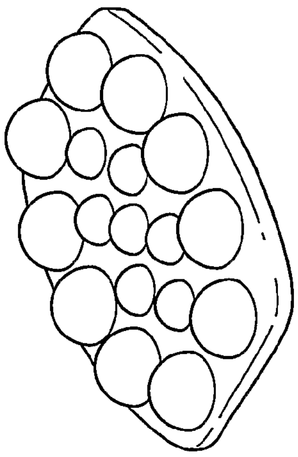
FIG. 2F is a perspective view of a sixth embodiment of a projection bar of the invention.

Ex. 5F has a multiplicity of hemispherical projections of different diameters as shown schematically in FIG. 2F.

Figure 2G:
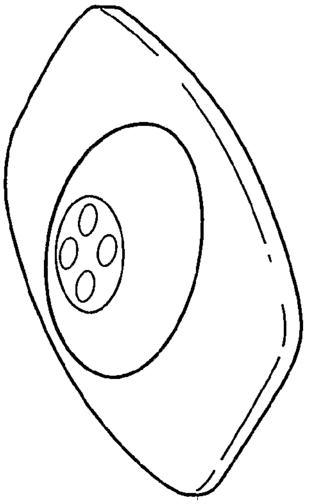
FIG. 2G is a perspective view of a seventh embodiment of a projection bar of the invention.

Ex. 5G has an elliptical projection that is embossed as shown schematically in FIG. 2G.

TABLE 5

| Geometrical characteristics of various articles used for cleansing | | | | | | | |
|---|---|---|---|---|---|---|---|
| GEOMETRIC CHARACTERISTICS | Ex. 5A | Ex. 5B | Ex. 5C | Ex. 5D | Ex. 5E | Ex. 5F | Ex. 5G |
| Dimensions of first body (L × W × H), cm | 9.14 cm × 6.4 cm × 1.6 cm | 9.14 cm × 6.4 cm × 1.6 cm | 9.14 cm × 6.4 cm × 1.6 cm | 9.14 cm × 6.4 cm × 1.6 cm | 9.14 cm × 6.4 cm × 1.6 cm | 9.14 cm × 6.4 cm × 1.6 cm | 9.14 cm × 6.4 cm × 1.6 cm |
| Geometry of projections | Circular large Hemisphere | Elliptical Hemisphere | Short and long rectangular and triangular | Circular short and long, small and large cylinders | Circular small Hemisphere | Circular small and large Hemisphere | Single Elliptical hemisphere with embossing |
| Number of projections | 2 | 2 | 17 | 17 | 20 | 17 | 1 |
| Terminal surface area of projection, $cm^2$ | | | Small rectangles 0.84 $cm^2$; Medium rectangles 1.12 $cm^2$; Large rectangles | Large 2 $cm^2$, small 0.5 $cm^2$ each projection | | | |

TABLE 5-continued

| Geometrical characteristics of various articles used for cleansing | | | | | | | |
|---|---|---|---|---|---|---|---|
| GEOMETRIC CHARACTERISTICS | Ex. 5A | Ex. 5B | Ex. 5C | Ex. 5D | Ex. 5E | Ex. 5F | Ex. 5G |
| | | | 1.7 $cm^2$; triangular 0.85 $cm^2$ for each projection | | | | |
| Height of terminal surface above first body, cm | 1.5 cm | 1.3 cm | 1.0 and 1.2 cm | 1.0 and 1.2 cm | 0.6 cm | 0.5 and 0.8 cm | 1.30 cm |

Example 6

Further Illustrations of the Invention

This example illustrates project bars in which the composition of the surfactant mass of the first body is different from the surfactant mass of the projections. Examples Ex. 6A-Ex. 6E are a series of projection bars that have the same geometrical properties as given in Table 1B. The compositions of the surfactant mass of the projections are shown in Table 6A, while the compositions of the surfactant mass of the first body are shown in Table 6B. These projection bars were manufactured by stamping of side-by-side co-extruded billets corresponding to the compositions of the projections and the first body, and having the appropriate volumes and thicknesses to fill the respective cavity volumes of the mold used to prepare the samples of Example 1.

TABLE 6A

| Compositions of surfactant mass of projections | | | | | |
|---|---|---|---|---|---|
| | Ex. 6A | Ex. 6B | Ex. 6C | Ex. 6D | Ex. 6E |
| INGREDIENT | WEIGHT % | | | | |
| SURFACTANTS | | | | | |
| Anhydrous Sodium Soap (80 Tallow/20 PKO) | 0 | 0 | 0 | 79.5 | 0 |
| Anhydrous Sodium Soap (85 Tallow/15 PKO) | 70.0 | 0 | 7.5 | 0 | 0 |
| Anhydrous Sodium Soap (90 Tallow/10 PKO) | 0 | 80.0 | 0 | 0 | 0 |
| Anhidrous Sodium Soap (50 PO/35 POS/15 PKO) | 0 | 0 | 0 | 0 | 67.0 |
| Sodium Cocoyl Isethionate | 0 | 0 | 40.5 | 0 | 0 |
| Cocamidopropyl Betaine. Sodium Sulfate | 0 | 0 | 1.5 | 0 | 0 |
| PLASTICIZING AGENTS | | | | | |
| Isopropyl Palmitate | 0 | 2.0 | 0 | 0 | 0 |
| Isopropyl Myristate | 0 | 0.5 | 0 | 0 | 0 |
| Dimethicone | 1.0 | 0 | 0 | 0 | 0 |
| Palm kernel oil FA | 0 | 0 | 0 | 3.2 | 0 |
| Coconut Fatty Acid | 3.5 (via citric acid) | 0.5 | 3.5 | 0 | 1.25 |
| Stearic Acid | 0 | 0 | 21.5 | 0 | 0 |
| Sodium Isethionate | 0 | 0 | 4.5 | 0 | 0 |
| Sodium Stearate | 0 | 0 | 4.0 | 0 | 0 |
| Calcium Carbonate | 0 | 0 | 8.0 | 0 | |
| Propylene Glycol | 0 | 0 | 0 | 0 | 1.5 |
| TEA | 0 | 0 | 0 | 0 | 1.5 |
| PEG 600 | 4.0 | 0 | 0 | 0 | 0 |
| Glycerol | 1.45 | 0 | 0 | 2.0 | 4.0 |
| Sorbitol | 0 | 0 | 0 | 0 | 6.0 |
| OTHERS (sodium chloride, sodium citrate, exfoliating, seed oils/extracts, perfume, colorant, antioxidant, etc.) | To 100 | To 100 | To 100 | To 100 | To 100 |
| Color | White | Green | White | Pink | Peach |
| WATER | 12.4 | 13.5 | 5.0 | 13.5 | 13.5 |

TABLE 6B

Compositions of surfactant mass of first body in Example 6

| INGREDIENT | Ex. 6A | Ex. 6B | Ex. 6C | Ex. 6D | Ex. 6E |
|---|---|---|---|---|---|
| | WEIGHT % | | | | |
| SURFACTANTS | | | | | |
| Anhydrous Sodium Soap (65Tallow/35PKO) | 0 | 0 | 54.5 | 0 | 0 |
| Anhydrous Sodium Soap (85Tallow/15PKO) | 7.5 | 0 | 0 | 8.3 | 7.5 |
| Anhidrous Sodium Soap (50 PO/35POS/15PKO) | 0 | 80.0 | 0 | 0 | 0 |
| Sodium Cocoyl Isethionate | 50.5 | 0 | 20.5 | 49.5 | 40.5 |
| Cocamidopropyl Betaine | 2.6 | 0 | 0 | 0 | 1.5 |
| Sodium Alkylbenzene Sulfate | 0 | 0 | 0 | 2.0 | 0 |
| PLASTICIZING AGENTS | | | | | |
| Isopropyl Myristate | 0 | 1.0 | 0.5 | 0 | 0 |
| Dimethicone (name) | 0 | 0 | 0.5 | 0 | 0 |
| Palm kernal oil FA | 0 | 0 | 0 | 1.0 | 0 |
| Coconut Fatty Acid | 3.5 | 0.5 | 2.0 | 3.1 | 3.5 |
| Mineral Oil | 0 | 0 | 0 | 0.25 | 0 |
| DIFFERENTIATING INGREDIENTS | | | | | |
| Stearic Acid | 20.5 | 0 | 4.8 | 20.0 | 21.5 |
| Sodium Isethionate | 4.5 | 0 | 5.6 | 4.7 | 4.5 |
| Sodium Stearate | 3.0 | 0 | 0 | 3.0 | 4.0 |
| Calcium Carbonate | 0 | 0 | 0 | 0 | 8.0 |
| Glycerol | 0 | 1.0 | 0 | 0 | 0 |
| Sodium Chloride | 0.2 | 0.7 | 0.6 | 0.4 | 1.0 |
| Polyethylene beads | 0 | 0.5 | 0 | 0 | 0 |
| Bentonite particles | 0.5 | 0 | 0 | 0 | 1.0 |
| Color | White | Blue | Yellow | Green | Pink |
| Licorice extract | 0.1 | 0 | 0.25 | 0 | 0 |
| Agar Agar | 0.1 | 0.5 | 0 | 0 | 1.0 |
| Grape Seed Oil | 1.0 | 0.80 | 0.25 | 0.75 | 0.1 |
| Eucalyptus oil | | | | 0.5 | 0.1 |
| MINORS (perfume. colorant. antioxidant. etc) | 1.5 | 1.5 | 1.5 | 1.5 | 1.5 |
| WATER | To 100 | To 100 | To 100 | To 100 | To 100 |

The invention claimed is:

1. An article for treating the skin comprising;

a) a first body and one or a multiplicity of projections arising from at least one surface of the first body;

b) wherein the first body and the projections comprise extruded thermoplastic masses;

c) the masses including a surfactant suitable for contact with human skin;

d) wherein at least the projections include a plasticizing agent at a level sufficient to provide the proiections with a Plastic Index Value of at least 7 mm as measured in the Three Point Bending Test;

e) wherein the plasticizing agent is selected from ester oils, silicone oils, fatty acids, and mixtures thereof; and f) wherein the projections has an Intrinsic Wear Rate of less than about 31 as measured by the Controlled Rubbing Test.

2. The article according to claim 1 wherein the surfactant or surfactants of which the first body mass is comprised can be the same or different from the surfactant or surfactants of which the projections mass is comprised.

3. The article according to claim 1, wherein the surfactant or surfactants of which the first body mass and the projection mass and are comprised are selected from a soap, a syndet and a combination thereof.

4. The article according to claim 1 wherein the ester oil is selected from fatty acid monoesters and polyesters, mono-, di- and triglycerides, modified triglycerides, liquid polyesters, and mixtures thereof.

5. The article according to claim 1 wherein the silicone oil is selected from a polydiorganosiloxane, a hydrocarbon modified polydiorganosiloxane, polydiorganonosiloxane polyether copolyols, hydroxyl terminated polydiorganosiloxanes and mixtures thereof.

6. The article according to claim 1 wherein the ester oil is isopropyl myristate, the fatty acid is palm kernel oil fatty acid or coconut oil fatty acid or babasu oil fatty acid or lauric acid or myristic acid or mixtures thereof, and the silicone is dimethicone.

7. The article according to claim 1, wherein the plasticizing agent is present at a level of at least about 1% based on the total weight of the projection mass.

8. The article according to claim 1, wherein the projection or multiplicity of projections have an elevation above a surface defining an average surface of the first body of between about 5 mm and about 20 mm.

9. The article according to claim 1, made by an extrusion process followed by automated stamping wherein the rate of stamping is at least 25 articles per minute.

10. The article according to claim 1, which is used for the dual purpose of cleansing and massaging skin.

11. A process for manufacture of an article for personal care, the process comprising the steps of:

i) mixing a surfactant containing composition with a plasticizing agent to form a thermoplastic mass;

ii) extruding the thermoplastic mass to form a billet;

iii) stamping the billet formed in step ii) alone or optionally with additional material, in a mold that will produce an article comprising a first body and one or a number of projections arising from at least one surface of the first body, wherein the projection or projections are comprised of the thermoplastic mass formed in step ii); and iv) wherein the stamping step iii) produces articles at a rate of at least 25 articles per minute.

12. A process according to claim 11 wherein the thermoplastic mass has a Plastic Index Value of at least about 7 mm as measured by the Three Point Bending Test.

13. A process according to claim 11 wherein the mold produces a projection or projections having an elevation of about 5 mm to about 15 mm as measured from a surface defining an average surface of the first body.

14. A process according to claim 11 wherein the mold produces at least 10 projections per article.

15. A process according to claim 11 wherein the stamping step iii) produces articles at a rate of at least 25 articles per minute.

16. The article according to claim 1 wherein the plasticizing agent compound comprises ingredients selected from silicone, fatty acids monoesters, C12-C14 fatty acids or blends thereof.

17. A method of treating the skin by either cleansing or massaging or both cleansing and massaging the skin comprising rubbing the skin with the article of claim 1.

* * * * *